(12) United States Patent
Forthmann et al.

(10) Patent No.: US 7,346,142 B2
(45) Date of Patent: Mar. 18, 2008

(54) COMPUTED TOMOGRAPHY METHOD FOR THE RECONSTRUCTION OF OBJECT IMAGES FROM REAL AND FICTITIOUS MEASURED VALUES

(75) Inventors: Peter Forthmann, Hamburg (DE); Thomas Kohler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/571,905

(22) PCT Filed: Jul. 4, 2005

(86) PCT No.: PCT/IB2005/052215
§ 371 (c)(1),
(2), (4) Date: Jan. 10, 2007

(87) PCT Pub. No.: WO2006/008678
PCT Pub. Date: Jan. 26, 2006

(65) Prior Publication Data
US 2007/0280523 A1    Dec. 6, 2007

(30) Foreign Application Priority Data
Jul. 13, 2004    (EP) .................... 04103311

(51) Int. Cl.
*G06K 9/00*    (2006.01)
(52) U.S. Cl. .................... 378/4; 378/901; 382/131
(58) Field of Classification Search ........... 378/4–20, 378/901; 382/131
See application file for complete search history.

(56) References Cited

U.S. PATENT DOCUMENTS

| 6,292,526 B1 | 9/2001 | Patch |
| 2003/0174803 A1 | 9/2003 | Katsevich |

OTHER PUBLICATIONS

Defrise, M., et al.; Improved two-dimensional rebinning of helical cone-beam computerized tomography data using John's equation; 2003; Institute of Physics Publishing-Inverse Problems; vol. 19; pp. S41-S54.

John, F.; The ultrahyperbolic equation with four independent variables; 1938; Duke Mathematical Journal; vol. 4; pp. 300-322.

Katsevich, A.; Analysis of an exact inversion algorithm for spiral cone-beam CT; 2002; Phys. Med. Biol.; vol. 47; pp. 2583-2597.

Kudo, H., et al.; Exact and approximate algorithms for helical cone-beam CT; 2004; Phys. Med. Biol.; vol. 49; pp. 2913-2931.

Patch, S.; Computation of Unmeasured Third-Generation VCT Views from Measured Views; 2002; IEEE Transactions on Medical Imaging; 21(7)801-813.

Turbell, H.; Cone-Beam Reconstruction Using Filtered Backprojection-Dissertation No. 672; 2001; Linkoping Institute of Technology, Sweden-Dept. of Electrical Engineering.

*Primary Examiner*—Courtney Thomas
*Assistant Examiner*—Alexander H Taningco (57) ABSTRACT

The invention relates to a method of computed tomography wherein a radiation source moves relative to an examination zone along a helical trajectory and wherein the movement involves a rotation around a rotational axis and a shifting parallel to the rotational axis. During the movement, a detector unit acquires real measured values. Fictitious measured values are determined from the real measured values by solving John's equation for a virtual movement of the radiation source along an intersection ellipse. The intersection ellipse intersects the helical trajectory at an intersection point and is the intersection of a virtual cylindrical surface, on which the helical trajectory is situated, with an intersection plane that is defined by a tangent vector of the helical trajectory at the intersection point and a vector that is oriented perpendicular to the rotational axis. Finally, an image of the examination zone is reconstructed using the real and fictitious measured values.

6 Claims, 8 Drawing Sheets

COMPUTED TOMOGRAPHY METHOD FOR THE RECONSTRUCTION OF OBJECT IMAGES FROM REAL AND FICTITIOUS MEASURED VALUES

The invention relates to a computed tomography method, in which a radiation source that produces a cone-shaped bundle of rays moves relative to an object on a helical trajectory. A bundle of rays is passed through the object, and from the intensity of the bundle of rays on the other side of the object, dependent real measured values are acquired. From the real measured values, non-acquired, fictitious measured values are determined using John's equation, and an object image is reconstructed from the real and fictitious measured values. The invention furthermore relates to a computed tomography machine for implementing the method, as well as to a computer program to control the computed tomography machine.

A computed tomography method of the type named at the outset is disclosed in "Improved two-dimensional rebinning of helical cone-beam computerized tomography data using John's equation", M. Defrise, F. Noo and H. Kudo, Inverse Problems 19 (2003), p. 41-p. 54, Institute of Physics Publishing (referred to below as E1).

Viewed mathematically, the object can be described by an object function $f(x)$, wherein the object function states for example the absorption value of the object at the place x. The natural logarithm of a measured value can then, as we know, be viewed as the line integral of the object function along the beam assigned to this value. According to "The ultrahyperbolic equation with four independent variables", F. John, Duke Math. J., 4, 300-22, each of these line integrals must solve the partial differential equation published there for the first time, the so-called John's equation. Each measured value of an object must therefore be a solution of John's equation. So in E1, fictitious measured values are determined which approximately fulfil John's equation, with the real measured values being used as boundary conditions of John's equation. The approximations made in E1 do however lead to interfering image artifacts in the reconstructed object image.

It is therefore an object of the present invention to define a computed tomography method in which, using John's equation, fictitious measured values are obtained from the real measured values, wherein the distortion of the reconstructed object image through image artifacts is reduced in comparison with the familiar method mentioned above, so that object images of better quality are reconstructed.

This object in achieved through a computed tomography method with the following steps:

a) Production of a cone-shaped bundle of rays that passes through an examination zone and an object located therein, using a radiation source,
b) Production of a relative movement between the radiation source on the one hand and the examination zone on the other hand, which comprises a rotation around a rotational axis and a displacement parallel to the rotational axis, and which has the form of a helix,
c) Acquisition of real measured values which depend on the intensity in the bundle of rays on the other side of the examination zone, using a detector unit,
d) Determination of non-acquired, fictitious measured values from the real measured values, wherein assigned to each fictitious measured value is a fictitious beam which is emitted from a fictitious radiation source position, and wherein the determination of a fictitious measured value has the following steps:

Determination of an intersection point of the helix with an ortho straight line that stands orthogonally on the helix and runs through the fictitious radiation source position, Determination of an intersection ellipse between a fictitious cylindrical surface, on which the helix is arranged, and an ellipse plane that is defined by the tangent vector of the helix at the intersection point and by a vector that is oriented perpendicular to the rotational axis and starts from the intersection point, Determination of the fictitious measured value from the real measured values by solving John's equation for a movement of the radiation source relative to the examination zone along the intersection ellipse, e) Reconstruction of an object image from the real measured values and the fictitious measured values.

In the computed tomography method according to the invention, first of all an intersection ellipse is formed, wherein in determining a fictitious measured value, John's equation is solved for the case where the radiation source has moved during acquisition on the intersection ellipse. As will be explained in greater detail below, for determining a fictitious measured value, exclusively those measured values are required whose assigned beams are emitted from radiation source positions that are adjacent to the intersection point, wherein in this area, the progressions of the intersection ellipse and of the helix barely differ from one another, so that solving John's equation for a progression of the radiation source on the intersection ellipse in place of a progression on the helix leads to only minimal distortions in the reconstructed object image. At the same time, since it is assumed that the radiation source moves on the intersection ellipse, it is possible to determine a fictitious measured value without the approximations described in E1 in relation to John's equation being required, which relate to a movement of the radiation source on the helix. Compared with the method described in E1, this leads to a reduction of image artifacts and thus to improved quality of the reconstructed object image.

If within the scope of the invention, the phrase "the radiation source runs along the intersection ellipse" or similar phrases are used, it is respectively the movement of the radiation source along the edge of the intersection ellipse that is described.

If within the scope of the invention it is said that a measured value is assigned to a beam or a beam is assigned to a measured value, then the measured value has been produced through detection of the intensity of the assigned beam.

The determination of the fictitious measured values as claimed in claims 2 to 4 leads to a further improvement in image quality.

A computed tomography machine for carrying out the method according to the invention is described in claim 5. Claim 6 defines a computer program for controlling a computed tomography machine as claimed in claim 5.

These and other aspects of the invention are apparent from and will be elucidated with reference to the embodiment described hereinafter.

Figure 1:
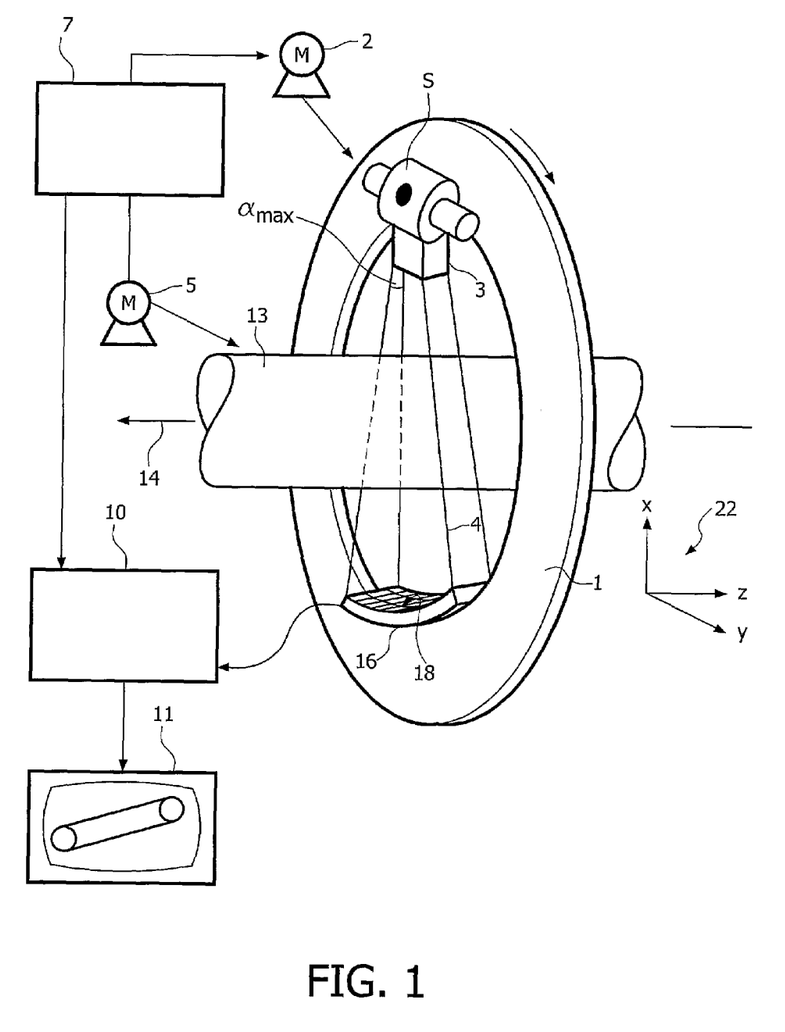
FIG. 1 shows a computed tomography machine with which the method according to the invention can be executed.

The computed tomography machine shown in FIG. 1 comprises a gantry 1 that can rotate around a rotational axis 14 that runs parallel to the z direction of the coordinate system 22 shown in FIG. 1. For this, the gantry 1 is driven by a motor 2 with a preferably constant but adjustable angular velocity. Affixed to the gantry 1 is a radiation source S, for example an X-ray emitter. This is equipped with a collimator arrangement 3 which, from the radiation produced by the radiation source S, collimates a cone-shaped bundle of rays 4, i.e. a bundle of rays which in both the z direction and in a direction perpendicular to that (i.e. in a plane that is perpendicular to the rotational axis) has a finite extension that is other than zero.

The bundle of rays 4 penetrates through a cylindrical examination zone 13, in which an object, e.g. a patient on a patient positioning table (neither of which are shown) or also a technical object, can be located. After passing through the examination zone 13, the bundle of rays 4 strikes a detector unit 16, affixed to the gantry 1, with a detector surface 18 that comprises numerous detector elements which in this embodiment are arranged in lines and columns, in the form of a matrix. The detector columns run parallel to the rotational axis 14. The detector lines are located in planes that are perpendicular to the rotational axis, in this embodiment on a circular arc around the radiation source S (focus-centered detector surface). In other embodiments, however, they can also be shaped differently, e.g. they can describe a circular arc around the rotational axis 14 or be a straight line. Each detector element hit by the bundle of rays 4 supplies, in each radiation source position, a measured value for a beam from the bundle of rays 4.

The angle of beam spread, designated by $\alpha_{max}$, of the bundle of rays 4 determines the diameter of the object cylinder within which the object to be examined is located during the acquisition of the measured values. Here, the angle of beam spread is defined as the angle which a beam lying in a plane that lies perpendicular to the rotational axis 14, at the edge of the bundle of rays 4, encloses with a plane defined by the radiation source S and the rotational axis 14.

The examination zone 13 or the object or the patient positioning table can be displaced by means of a motor 5 parallel to the rotational axis 14 or to the z axis. Equivalent to this, however, the gantry could be displaced in this direction. If it is a technical object and not a patient, the object can be rotated in the course of an examination whilst the radiation source S and the detector unit 16 stand still.

When the motors 2 and 5 run simultaneously, the radiation source S and the detector unit 16 describe a helical trajectory 17 relative to the examination zone 13. On the other hand, when the motor 5 for advancing in the direction of the rotational axis 14 stands still and the motor 2 allows the gantry to rotate, the result is a circular trajectory for the radiation source S and the detector unit 16 relative to the examination zone 13. Only the helical trajectory is discussed below.

The measured values acquired by the detector unit 16 are supplied to a computing unit 10 which is connected to the detector unit 16, e.g. via a data transmission unit (not shown) that works in a contactless manner. The computing unit 10 determines fictitious measured values, reconstructs the absorption distribution in the examination zone 13, and reproduces it, for example on a monitor 11. The two motors 2 and 5, the computing unit 10, the radiation source S and the transfer of the measured values from the detector unit 16 to the computing unit 10 are controlled by a control unit 7.

In other embodiments, the acquired measured values for reconstruction can first of all be supplied to one or more reconstruction computers which pass on the reconstructed data, e.g. via a glass fiber cable, to the image processing computer.

Figure 2:
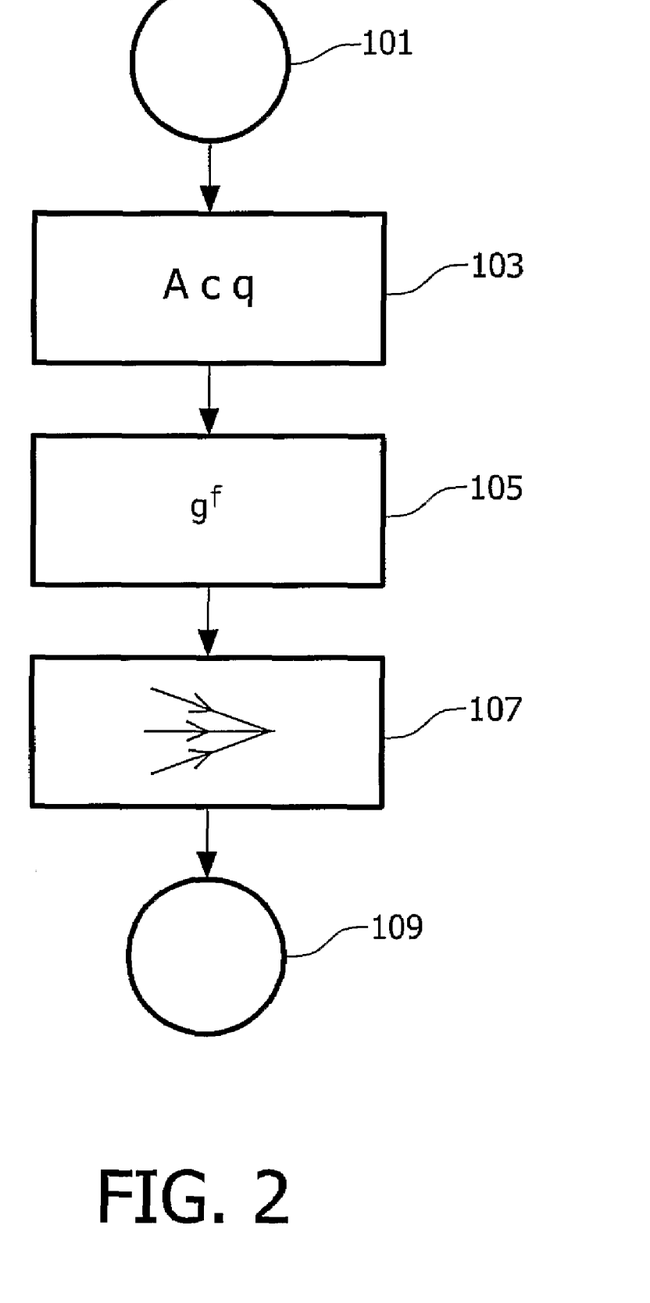
FIG. 2 shows a flow chart for the method according to the invention.

The individual steps of an embodiment of the computed tomography method according to the invention are explained below on the basis of the flow chart in FIG. 2.

After the initialization in step 101, the gantry rotates at an angular velocity which in this design example is constant. It can however also vary, e.g. depending on the time or on the radiation source position.

In step 103, the examination zone or the patient positioning table is shifted parallel to the rotational axis 14 and the radiation of the radiation source S is switched on, so that the detector unit 16 can detect the radiation from numerous angular positions s and the radiation source S moves relative to the examination zone 13 on the helical trajectory 17. In this way, the real measured values are acquired.

The helix 17 can be parameterized by the following equation:

$$y(s) = \begin{pmatrix} R\cos s \\ R\sin s \\ s\dfrac{h}{2\pi} \end{pmatrix} \quad (1)$$

Here, s is the angular position of the radiation source on the helix. Furthermore, h is the pitch, i.e. the distance between two adjacent coils in the direction of the rotational axis 14, and R is the radius of the helix.

In step 105, fictitious measured values are determined from the acquired real measured values, using John's equation. The individual steps in the determination of a fictitious measured value are described below, in connection with the flow chart in FIG. 3.

Figure 3:
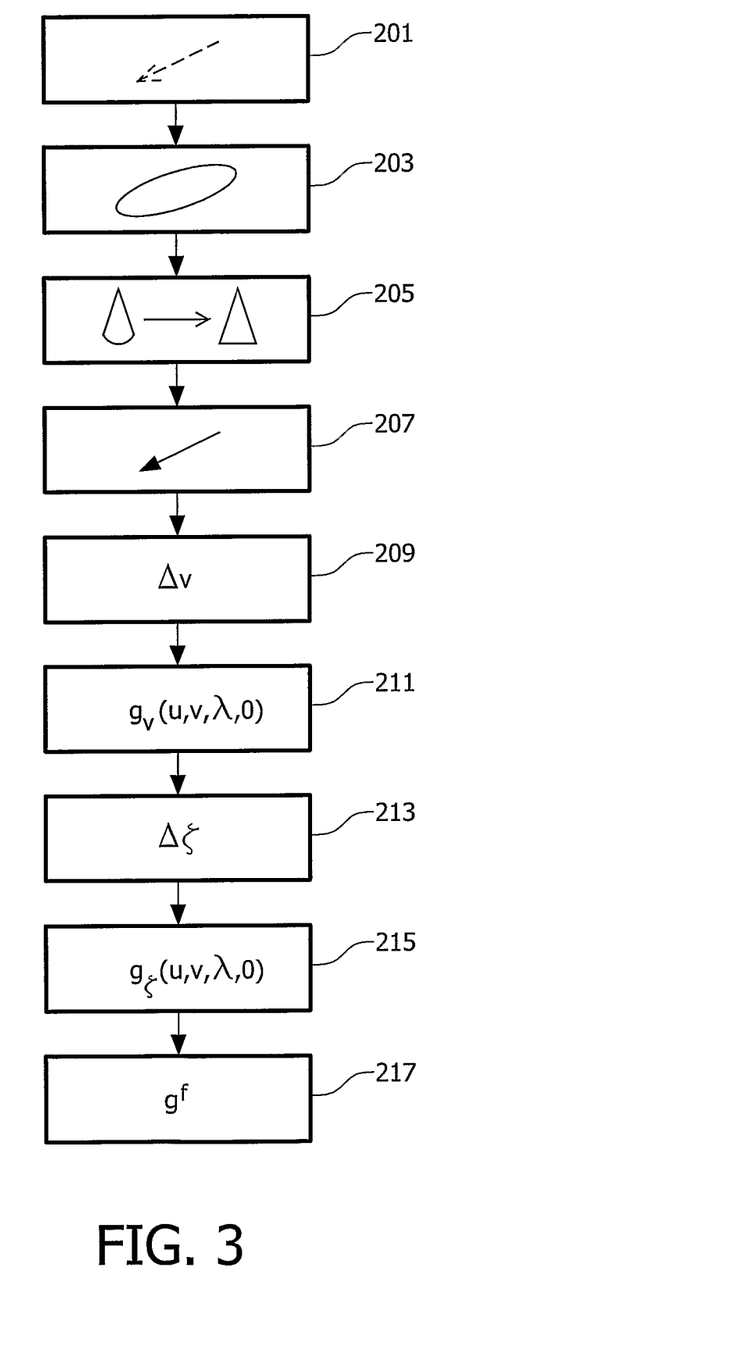
FIG. 3 shows a flow chart for a determination of a fictitious measured value, according to the invention.

First of all, in step 201 a fictitious beam, i.e. a fictitious radiation source position 52 from which the fictitious beam is emitted, and a beam direction are specified for which a fictitious measured value is to be determined. For preference, the fictitious radiation source position lies on a fictitious cylinder surface 39 on which the helix 17 runs (see FIG. 6).

Figure 4:
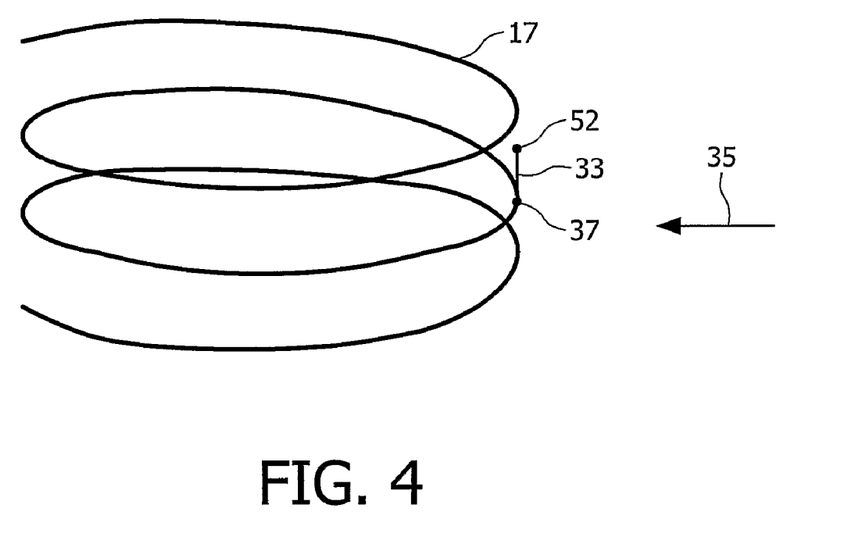
FIG. 4 shows a schematic representation of a helix on which a radiation source moves, and a real and a fictitious radiation source position that lie on an ortho straight line.
Figure 5:
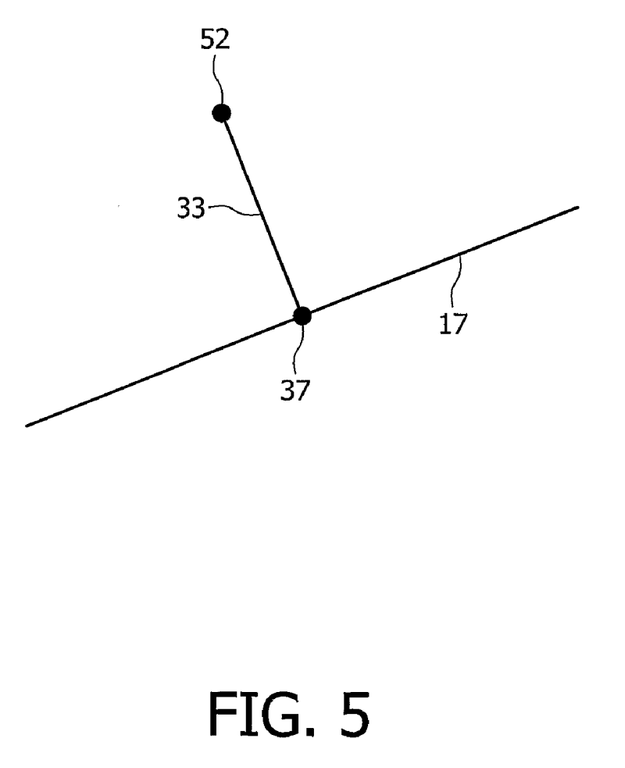
FIG. 5 shows a schematic side view of a portion of the helix, the fictitious and real radiation source positions, and the ortho straight line from FIG. 4.

In step 203, an intersection ellipse 45 is determined for the fictitious beam. For this, first of all an ortho straight line 33, which stands orthogonally on the helix 17 and runs through the fictitious radiation source position 52, and an intersection point 37 of this ortho straight line 33 with the helix 17, are determined. This is shown in FIGS. 4 and 5, wherein in FIG. 5, a portion of the helix 17 is shown, viewed in the direction 35 (see FIG. 4).

Figure 6:
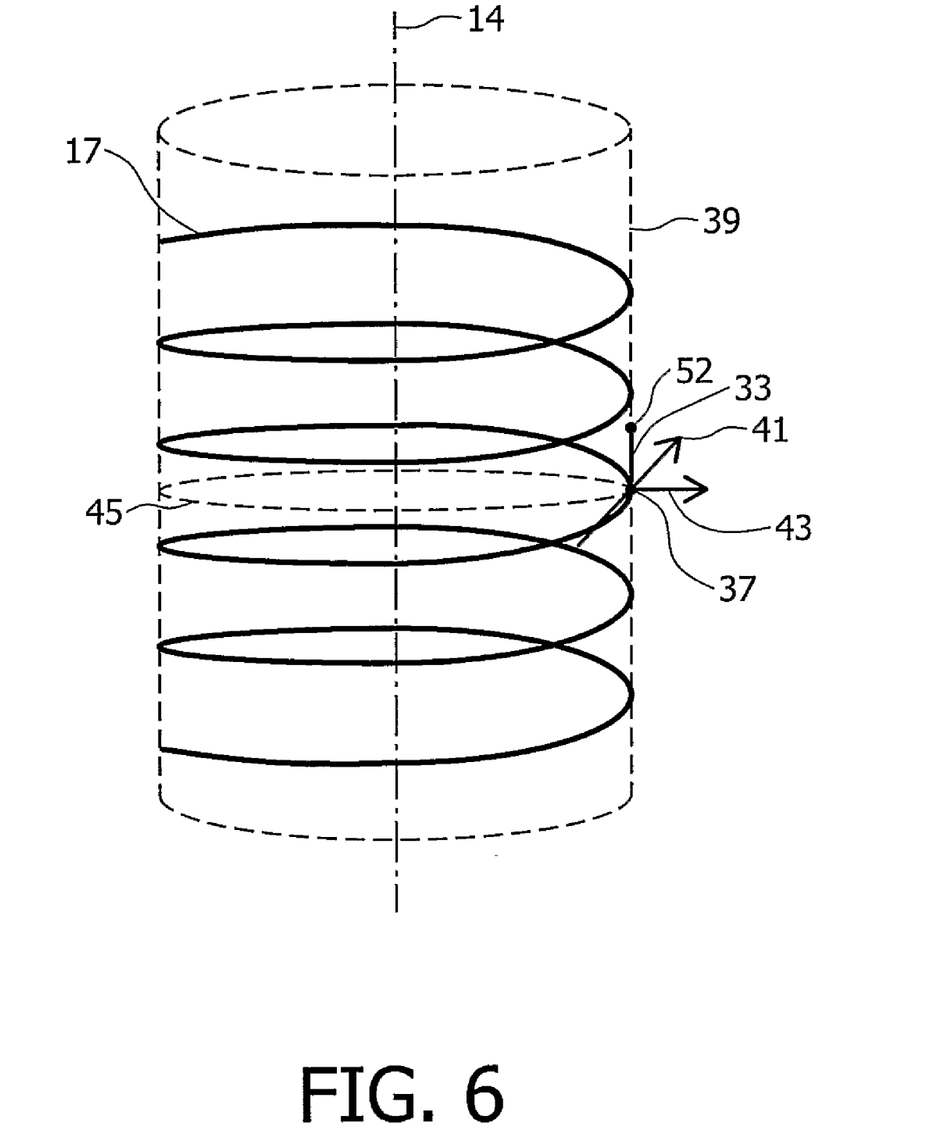
FIG. 6 shows a schematic representation of the helix that runs on a fictitious cylindrical surface, and of an intersection ellipse.

The helix 17 runs on a fictitious cylindrical surface 39 (see FIG. 6). The intersection ellipse 45 is the intersection of this cylindrical surface 39 with a plane that is defined by the tangent vector 41 of the helix 17 at the intersection point 37 and by a vector 43 which, starting from the intersection point, is oriented perpendicular to the rotational axis 14. The intersection ellipse 45 thus lies in this plane.

In step 205, the real measured values whose assigned rays are emitted from the intersection point 37, are projected onto a virtual planar detector surface 47 along these rays.

Figure 7:
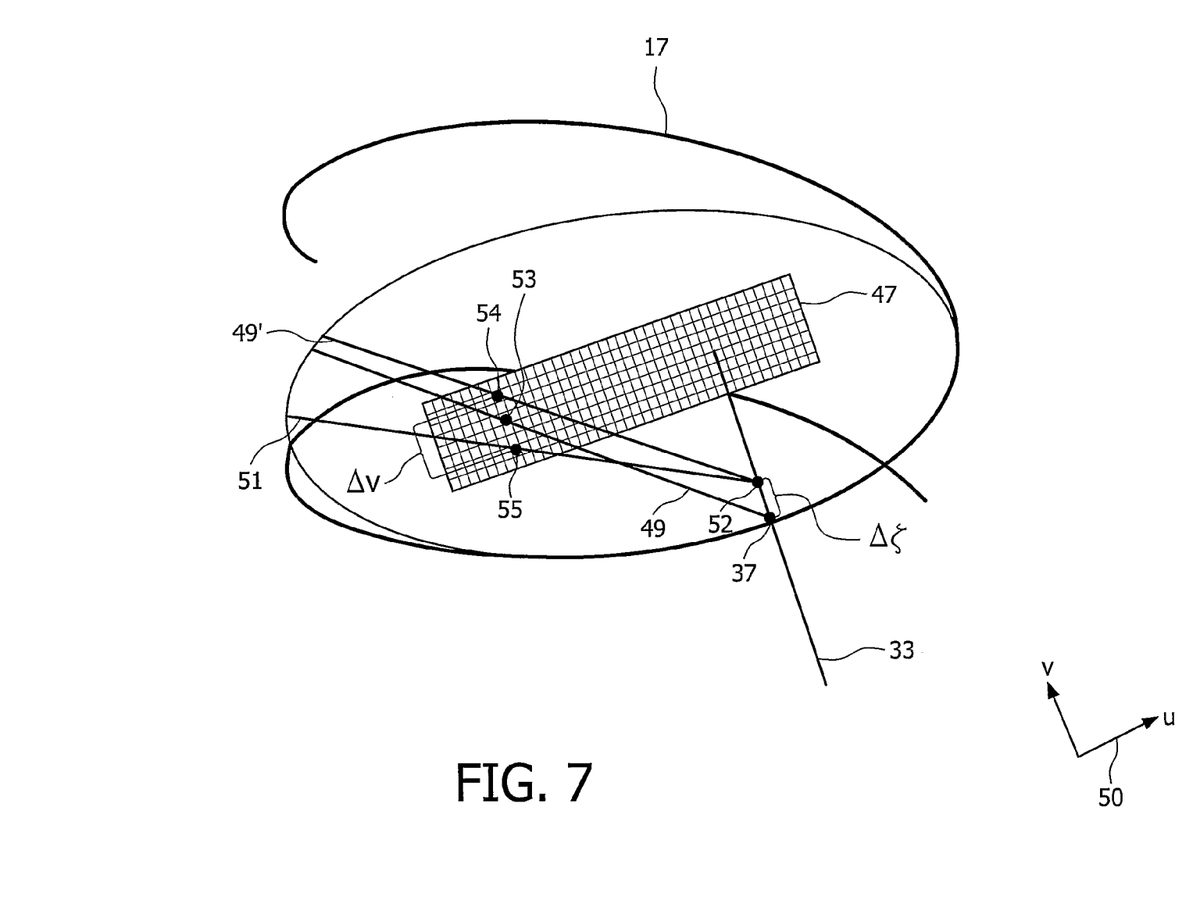
FIG. 7 shows a portion of the helix, the intersection ellipse, and a virtual planar detector surface.

The virtual planar detector surface 47 is at least as large and dimensioned such that all real beams which—starting from the intersection point 37—strike the real detector surface 18, the fictitious beam 51 specified in step 201, and the displaced beam 49' described below, intersperse the virtual planar detector surface 47 (see FIG. 7). Furthermore, the virtual planar detector surface 47 is oriented so that it is orthogonal to the ellipse plane (the plane in which the intersection ellipse 45 lies). The virtual detector surface 47 has detector elements arranged in detector lines and detector columns, wherein the detector lines are arranged such that they run parallel to the ellipse plane. The detector columns run orthogonally to the ellipse plane. A position on the planar detector surface 47 is defined by the coordinates (u,v) of the (u, v) coordinate system 50, wherein the u coordinate axis runs parallel to the detector lines and the v coordinate axis runs parallel to the detector columns. For reasons of clarity, in FIG. 7 the (u, v) coordinate system is shown below the planar detector surface 47, although the coordinate system 50 naturally lies on the planar detector surface 47.

In step 207, a real beam 49 is determined, assigned to which is an acquired real measured value, and which is emitted from the intersection point 37, and whose impingement point 53 on the planar detector surface 47 lies on the same straight line oriented parallel to the ortho straight line 33 as the impingement point 55 of the virtual beam 51 on the planar detector surface 47. This means that the impingement points 53, 55 of the real beam 49 and the fictitious beam 51 lie in the same detector column of the virtual planar detector surface 47.

In the following steps, the fictitious measured value $g^f$ is calculated using a Taylor development (equation (2)) and John's equation:

$$g^f = g(u_\alpha, v_\alpha, \lambda_\alpha, 0) + \Delta\zeta \cdot g_\zeta(u_\alpha, v_\alpha, \lambda_\alpha, 0) + \Delta v \cdot g_v(u_\alpha, v_\alpha, \lambda_\alpha, 0). \quad (2)$$

Here, $g^f$ is the fictitious measured value of the fictitious beam 51 specified in step 201. Furthermore, $g(u_\alpha, v_\alpha, \lambda_\alpha, 0)$ is the real measured value that is produced by the real beam 49 determined in step 207. The real beam 49 is emitted from the real radiation source position 37 with the angular position $\lambda_\alpha$ on the intersection ellipse 45, i.e. from the intersection point 37, and strikes the virtual planar detector surface 47 at the place $(u_\alpha, v_\alpha)$. The distance $\Delta\zeta$ is the distance between the fictitious radiation source position 52 and the real radiation source position 37. The distance $\Delta v$ is the distance between the impingement point 55 of the fictitious beam 51 on the virtual detector surface 47 and an impingement point 54 of a displaced beam 49' on the virtual detector surface 47, wherein the displaced beam 49' is emitted from the fictitious radiation source position 52 and runs parallel to the real beam 49.

A movement of a radiation source on the intersection ellipse 45 can be parameterized in the ellipse plane by $y_e(\lambda) = (R_1 \cos \lambda, R_2 \sin \lambda)$, with $R_1$ being half the large axis and $R_2$ half the small axis of the intersection ellipse 45. The parameter $\lambda$ is the angular position of the radiation source on the intersection ellipse 45, wherein $\lambda_\alpha$ is the angular position of the intersection point 37.

In step 209, the distance $\Delta v$ between the impingement points 54, 55 of the fictitious [beam] 51 and of the displaced beam 49' on the virtual planar detector surface 47 is determined.

In step 211, the acquired real measured values are partially derived according to the variable v at the place $(u_\alpha, v_\alpha, \lambda_\alpha, 0)$. The partial derivation according to v at the place $(u_\alpha, v_\alpha, \lambda_\alpha, 0)$ is described by $g_v(u_\alpha, v_\alpha, \lambda_\alpha, 0)$. The partial derivation can for example be carried out with the familiar method of finite differences.

In step 213, the distance $\Delta\zeta$ is determined, i.e. the distance between the real [intersection point] 37 and the fictitious radiation source position 52 along the ortho straight line 33.

In step 215, the partial derivation of the real measured values is calculated according to the real radiation source position on the ortho straight line 33 at the place $(u_\alpha, v_\alpha, \lambda_\alpha, 0)$. This partial derivation is described by $g_\zeta(u_\alpha, v_\alpha, \lambda_\alpha, 0)$. A problem here is that whilst there is a real radiation source position on the ortho straight line 33 at the intersection point 37, there are no further real radiation source positions on the ortho straight line 33. For this reason, the partial derivation $g_\zeta(u_\alpha, v_\alpha, \lambda_\alpha, 0)$ is obtained, using John's equation, for a movement of the radiation source relative to the object along the intersection ellipse 45. For such a relative movement, John's equation is as follows:

$$R_1 R_2 g_{u\zeta}(u_\alpha, v_\alpha, \lambda_\alpha, 0) - 2u g_v(u_\alpha, v_\alpha, \lambda_\alpha, 0) - (R_1 R_2 + u^2) g_{uv}(u_\alpha, v_\alpha, \lambda_\alpha, 0) - R_2 g_{\lambda v}(u_\alpha, v_\alpha, \lambda_\alpha, 0) - u v g_{vv}(u_\alpha, v_\alpha, \lambda_\alpha, 0) = 0. \quad (3)$$

Here, $g_{u\zeta}(u_\alpha, v_\alpha, \lambda_\alpha, 0)$ is the partial derivation according to the variables u and $\zeta$ at the place $(u_\alpha, v_\alpha, \lambda_\alpha, 0)$, i.e. $g_{u\zeta}(u_\alpha, v_\alpha, \lambda_\alpha, 0) = \partial^2 g(u_\alpha, v_\alpha, \lambda_\alpha, 0)/(\partial u \partial \zeta)$. Accordingly, $g_{uv}(u_\alpha, v_\alpha, \lambda_\alpha, 0)$ is the partial derivation according to the variables u and v at the place $(u_\alpha, v_\alpha, \lambda_\alpha, 0)$, i.e. $g_{uv}(u_\alpha, v_\alpha, \lambda_\alpha, 0) = \partial^2 g(u_\alpha, v_\alpha, \lambda_\alpha, 0)/(\partial u \partial v)$. Furthermore, $g_{\lambda v}(u_\alpha, v_\alpha, \lambda_\alpha, 0)$ is the partial derivation according to the variables $\lambda$ and v at the place $(u_\alpha, v_\alpha, \lambda_\alpha, 0)$, i.e. $g_{\lambda v}(u_\alpha, v_\alpha, \lambda_\alpha, 0) = \partial^2 g(u_\alpha, v_\alpha, \lambda_\alpha, 0)/(\partial \lambda \partial v)$. Finally, $g_{vv}(u_\alpha, v_\alpha, \lambda_\alpha, 0)$ is the second partial derivation according to the variable v, i.e. $g_{vv}(u_\alpha, v_\alpha, \lambda_\alpha, 0) = \partial^2 g(u_\alpha, v_\alpha, \lambda_\alpha, 0)/\partial^2 v$.

The variable $\zeta$ of a beam parameterized by $(u, v, \lambda, \zeta)$ describes different radiation source positions on the ortho straight line 33.

If, within the framework of the invention, a derivation is to be formed of the real measured values according to a position on a straight line, for example according to the radiation source position on the ortho straight line 33 or according to the position of the impingement point of a beam on the detector surface along a straight line that is oriented parallel to the ortho straight line, the direction on the respective straight line into which derivation is to take place can be freely chosen. However, the selected directions cannot be altered during the entire calculation of the fictitious measured values.

Through integration via the variable u, John's equation (3) can be solved according to $g_\zeta(u_\alpha, v_\alpha, \lambda_\alpha, 0)$.

$$g_\zeta(u_\alpha, v_\alpha, \lambda_\alpha, 0) = \frac{R_1 R_2 + u_\alpha^2}{R_1 R_2} g_v(u_\alpha, v_\alpha, \lambda_\alpha, 0) + \frac{1}{R_1} \int du' \left( g_{\lambda v}(u', v_\alpha, \lambda_\alpha, 0) + \frac{u' v_\alpha}{R_1 R_2} g_w(u', v_\alpha, \lambda_\alpha, 0) \right) \quad (4)$$

Figure 8:
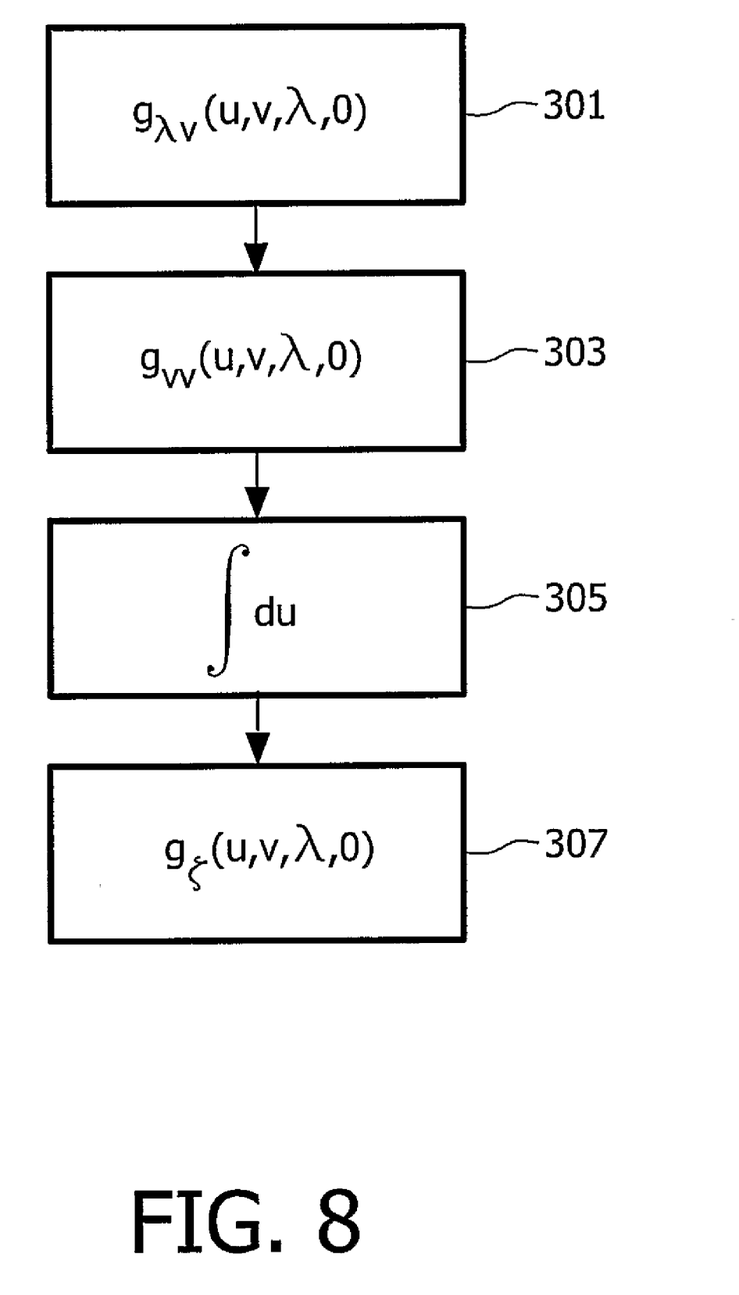
FIG. 8 shows a flow chart of a method according to the invention, to determine a partial derivation of the real measured values.

In the following, on the basis of the flow chart shown in FIG. 8, it will be explained how, according to equation (4), the partial derivation $g_\zeta(u_\alpha,v_\alpha,\lambda_\alpha,0)$ is determined.

In step 301, the partial derivation $g_{\lambda v}(u,v_\alpha,\lambda_\alpha,0)$ is calculated. For this, the real measured values are first of all partially derived according to the angular position λ of the radiation source on the intersection ellipse 45. A problem here is that during acquisition, the radiation source has moved not on the intersection ellipse 45, but on the helix 17. The helix 17 and the intersection ellipse 45 touch one another at the intersection point 37, so that on the intersection ellipse 45 there is only one real radiation source position with the angular position $\lambda_\alpha$. For this reason, for an angular range arranged around the intersection point 37, it is assumed that a beam that has been emitted during acquisition from a real radiation source position on the helix 17 has been emitted from the intersection ellipse 45. That is, a radiation source position which on the helix 17 is distant from the intersection point by the angle Δs is regarded as if this radiation source position had lain on the intersection ellipse 45 during acquisition, with this radiation source position being distant from the intersection point 37 on the intersection ellipse by the angle Δλ=Δs. This approximation hardly ever leads to errors in the ultimately reconstructed object image, since in step 203, the intersection ellipse 45 has been determined in such a way that its tangent vector and the tangent vector 41 of the helix 17 at the intersection point 37 are the same, i.e. in the area of the intersection point 37, the intersection ellipse 45 and the helix 17 have almost the same course. Thus for partial derivation according to the angular position λ, only some assumed radiation source positions on the intersection ellipse 45, i.e. only some angular positions λ, are looked at which lie in an angle range of a few degrees around the intersection point 37. This angle range can be up to 1°, 2°, 5°, 10°, 15° or 20°. The angular position $\lambda_\alpha$ of the intersection point 37 preferably lies in the middle of the respective angle range. Furthermore, it is assumed that the virtual detector surface 47 defined in step 205 rotates with the radiation source. This means that when one views a radiation source position that has been displaced in the angle range in relation to the intersection points 37 by Δλ on the intersection ellipse 45, the measured values are projected onto the virtual detector surface 47 that was defined in step 205 and was rotated by Δλ around the rotational axis 14, and are viewed there. The partial derivation according to the angular position λ on the intersection ellipse 45 can, as has been mentioned above, be carried out for example with the aid of the method of finite differences.

After the measured values have been partially derived according to the angular position λ, the second derivation of the real measured values according to the variable v at the place $(u_\alpha,v_\alpha,\lambda_\alpha,0)$ is formed $(g_{vv}(u_\alpha,v_\alpha,\lambda_\alpha,0))$. Here, only those real measured values are considered whose assigned beams are emitted from the intersection point 37. These real measured values are thus twice partially derived according to the variable v, for example with the method of finite differences.

In step 305, integration is carried out according to equation (4).

For this, first of all a first total is formed, in that those measured values partially derived in step 301 are added up whose beams are emitted from the intersection point 37 and strike the detector line, defined by the variable $v_\alpha$, of the virtual planar detector surface 47. That is, the partial derivations of those real measured values are added up whose assigned beams are emitted from the intersection point 37 and pass through the virtual detector surface 47 on a straight line that runs parallel to the ellipse plane and through the impingement point 53 of the real beam 49 defined in step 207. The resulting first total is multiplied by a first weighting factor that is proportional to the reciprocal value of half the large axis $R_1$ of the intersection ellipse 45, and in particular is equal to this reciprocal value.

Furthermore, in step 305 a second total is formed in that those measured values $g_{vv}(u_\alpha,v_\alpha,\lambda_\alpha,0)$ that were partially derived in step 303, whose beams are emitted from the intersection point 37 and strike the detector line, defined by the variable $v_\alpha$, of the virtual planar detector surface 47, are respectively first of all multiplied by their respective u position and then added up. In other words, those partially derived real measured values, multiplied by their respective u position, are added up whose assigned beams are emitted from the intersection point 37 and pass through the virtual detector surface 47 on a straight line that runs parallel to the ellipse plane and through the impingement point 53 of the real beam 49 defined in step 207. The resulting second total is multiplied by a second weighting factor that is proportional to the reciprocal value of half the small axis $R_2$ of the intersection ellipse 45, to the reciprocal value of the square of half the large axis $R_1$ of the intersection ellipse 45, and to the v position $v_\alpha$ of the respective derived real measured value on the virtual detector surface 47. Preferably, the second weighting factor is equal to the product of the reciprocal value of half the small axis $R_2$ of the intersection ellipse 45, the reciprocal value of the square of half the large axis $R_1$ of the intersection ellipse 45 and the v position $v_\alpha$ of the respective derived real measured value on the virtual detector surface 47.

Finally in step 307, the desired partial derivation $g_\zeta(u_\alpha, v_\alpha,\lambda_\alpha,0)$ is calculated. For this, the partial derivation $g_v(u_\alpha, v_\alpha,\lambda_\alpha,0)$ formed in step 211 is multiplied at the place $(u_\alpha,v_\alpha,\lambda_\alpha,0)$ by a third weighting factor that is proportional to the reciprocal value of half the small axis $R_2$ of the intersection ellipse 45, to the reciprocal value of half the large axis $R_1$ of the intersection ellipse 45, and to the sum of the product of the two half axes $R_1$, $R_2$ of the intersection ellipse 45 and of the square of the u position $v_\alpha$ of the real measured value on the virtual detector surface 47. Preferably, the third weighting factor is equal to the product of the reciprocal value of half the small axis $R_2$ of the intersection ellipse 45, the reciprocal value of half the large axis $R_1$ of the intersection ellipse 45, and of the sum of the product of the two half axes $R_1$, $R_2$ of the intersection ellipse 45 and of the square of the u position $u_\alpha$ of the real measured value on the virtual detector surface 47.

The derivation value multiplied by the third weighting factor is finally added to the first total that has been multiplied by the first weighting factor, and to the second sum total has been multiplied by the second weighting factor, for partial derivation $g_\zeta(u_\alpha,v_\alpha,\lambda_\alpha,0)$ in accordance with equation (4).

After the partial derivation $g_\zeta(u_\alpha,v_\alpha,\lambda_\alpha,0)$ has been calculated, the fictitious measured value $g^f$, which has been caused by the fictitious beam 51 specified in step 201, is calculated in accordance with equation (2) in step 217.

For this, the real measured value $g(u_\alpha,v_\alpha,\lambda_\alpha,0)$ to which the real beam 49 determined in step 207 is assigned, the product of the distance $\Delta\zeta$ between the intersection point 37 and the virtual radiation source position 52 and the partial derivation $g_\zeta(u_\alpha,v_\alpha,\lambda_\alpha,0)$, determined in step 215, of the real measured values at the place $(u_\alpha,v_\alpha,\lambda_\alpha,0)$, and the product of the distance $\Delta v$ of the impingement points 54, 55 of the fictitious [beam] 51 and of the displaced beam 49' on the virtual planar detector surface 47 with the partial derivation $g_v(u_\alpha,v_\alpha,\lambda_\alpha,0)$, determined in step 211, of the real measured values at the place $(u_\alpha,v_\alpha,\lambda_\alpha,0)$ are added, with the resulting sum being the fictitious measured value $g^f$.

The steps 201 to 217 can be repeated for further fictitious measured values, until a desired quantity of fictitious measured values has been determined.

After one or more fictitious measured values have been produced from the real measured values, in step 107 an object image is reconstructed by back projection of the real and fictitious measured values.

Figure 9:
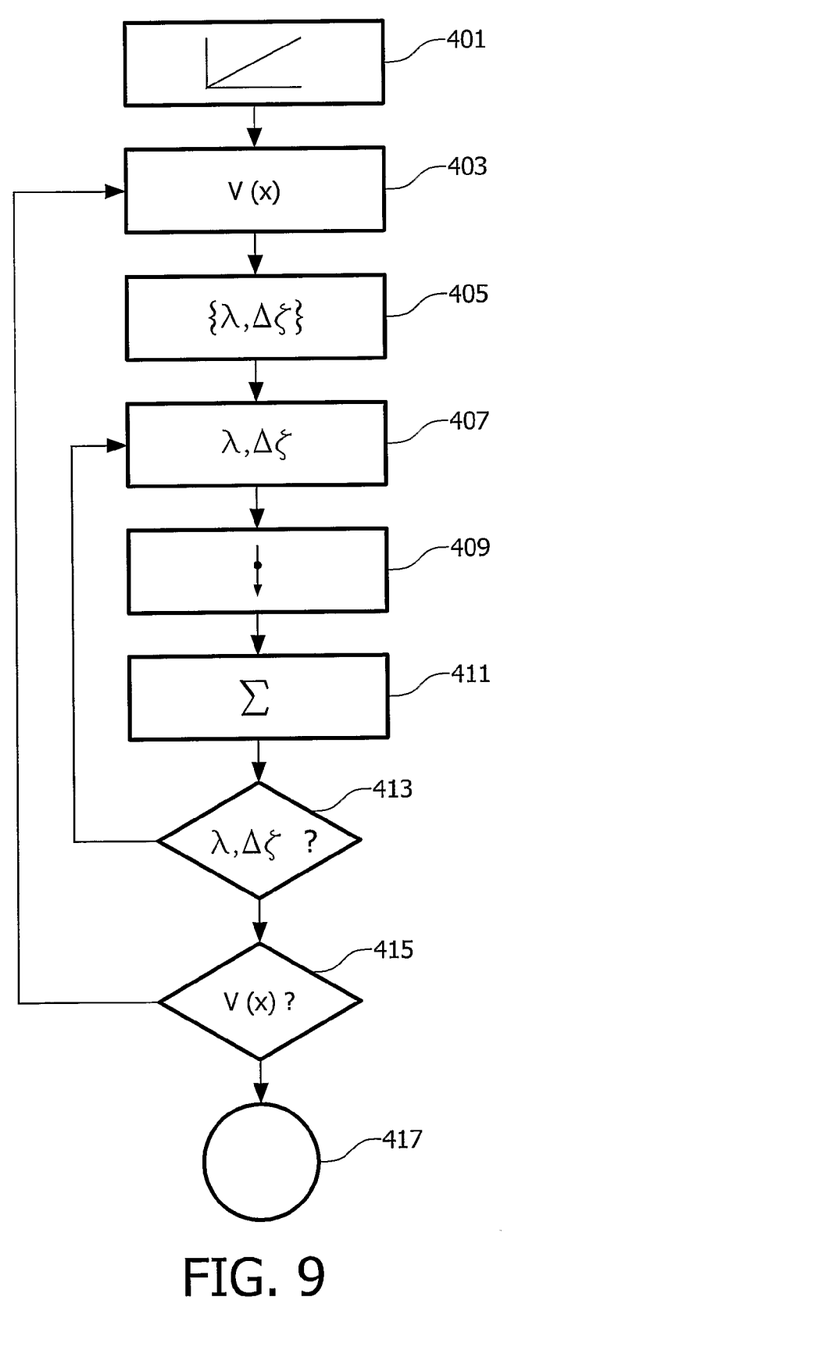
FIG. 9 shows a flow chart of a filtered back projection.

An embodiment of a back projection, which in this case is a known filtered back projection, is presented below on the basis of the flow chart shown in FIG. 9.

In step 401, the measured values (i.e. the real and the fictitious measured values) are filtered in the familiar way, with one-dimensional filtering with a ramp-shaped transmission factor, rising with the frequency, being applied (see for example "Bildgebende Verfahren in der Medizin" [Imaging methods in medicine], O. Dössel, Springer Verlag (2000)).

In step 403, a voxel $V(x)$ is specified at the place x in the object that has not yet been reconstructed.

In step 405, the quantity of measured values (real and fictitious) is determined whose assigned beams (real and fictitious) pass through the voxel $V(x)$.

Then in step 407, from the quantity determined in step 405, a measured value is specified that has not yet been used for the reconstruction of the voxel $V(x)$.

In step 409, it is checked whether the beam which is assigned to the measured value selected in step 407 passes centrally through the voxel $V(x)$. If this is not the case, then a central beam and the corresponding measured value is calculated through interpolation of adjacent measured values, for example by means of bilinear interpolation.

If the beam of the measured value specified in step 407 passes centrally through the voxel $V(x)$, then in step 411 this measured value is added to the voxel $V(x)$. Otherwise, the measured value obtained in step 409 through interpolation is added to the voxel $V(x)$.

In step 413, it is checked whether all measured values that have been established in step 405 have been taken into account in the reconstruction of the voxel $V(x)$. If this is the case, then we continue with step 407. Otherwise, step 415 follows.

In step 415 it is checked whether all voxels $V(x)$ of the object image have been reconstructed. If this is not the case, then we continue with step 403. Otherwise, the back projection ends at step 417.

The method according to the invention is thus ended at step 109.

The computed tomography method according to the invention can also be used in pi reconstruction. Pi reconstruction is essentially familiar, so that no further explanation of it is required here ("Cone-beam reconstruction using filtered backprojection", H. Turbell, dissertation, Linköping Institute of Technology, Sweden, 2001). In pi reconstruction, only those measured values are used that lie on the detector surface 18 in a range that is described as a pi window. The pi window is not described in further detail here either, since it is known for example from the publication named above. Measured values that lie outside the pi window are not taken into account in the pi reconstruction. With the method described in steps 201 to 217 in particular, from acquired measured values that do not lie in the pi window, fictitious measured values can be determined that lie in the pi window. Thus more measured values are available for pi reconstruction, through which the signal/noise ratio is improved.

The computed tomography method according to the invention is not restricted to the reconstruction methods named here. Any reconstruction method that uses both the acquired real measured values and the fictitious measured values can be applied within the scope of the invention.

REFERENCE KEY $\alpha_{max}$ Angle of beam spread
$\Delta\zeta$ Distance between the fictitious radiation source position and the real radiation source position
$\Delta v$ Distance between the impingement point of the fictitious beam on the virtual planar detector surface and the impingement point of the shifted beam on
S Radiation source
1 Gantry
2, 5 Motor
3 Collimator arrangement
4 Bundle of rays
7 Control unit
10 Computing unit
11 Monitor
13 Examination area
14 Rotational axis
16 Detector unit
17 Helical trajectory
18 Detector surface
22 (x,y,z) coordinate system
33 Ortho straight line
35 Direction in FIG. 4
37 Intersection point of the ortho straight line with the helical trajectory
39 Fictitious cylindrical surface
41 Tangent vector
43 Vector orientated perpendicular to the rotational axis
45 Intersection ellipse
47 Virtual planar detector surface
49 Realbeam
49' Displaced real beam
50 (u,v) coordinate system
51 Fictitious beam
52 Fictitious radiation source position
53 Impingement point of the real beam on the virtual planar detector surface
54 Impingement point of the shifted real beam on the virtual planar detector surface
55 Impingement point of the virtual beam on the virtual planar detector surface

The invention claimed is:

1. A computed tomography method with the following steps:
   a) Production of a cone-shaped bundle of rays which passes through an examination zone and an object located therein, using a radiation source,
   b) Production of a relative movement between the radiation source on the one hand and the examination zone on the other hand, which comprises a rotation around a rotational axis and a displacement parallel to the rotational axis, and which has the form of a helix, c) Acquisition of real measured values which depend on the intensity in the bundle of rays on the other side of the examination zone, using a detector unit, d) Determination of non-acquired, fictitious measured values from the real measured values, wherein assigned to each fictitious measured value is a fictitious beam which is emitted from a fictitious radiation source position, and wherein the determination of a fictitious measured value has the following steps:

Determination of an intersection point of the helix with an ortho straight line that stands orthogonally on the helix and runs through the fictitious radiation source position, Determination of an intersection ellipse between a fictitious cylindrical surface, on which the helix is arranged, and an ellipse plane that is defined by the tangent vector of the helix at the intersection point and by a vector that is oriented perpendicular to the rotational axis and starts from the intersection point, Determination of the fictitious measured value from the real measured values by solving John's equation for a movement of the radiation source relative to the examination zone along the intersection ellipse, e) Reconstruction of an object image from the real measured values and the fictitious measured values.

2. A method as claimed in claim 1, wherein in step d), determination of the fictitious measured value comprises the following steps:

i) Definition of a virtual planar detector surface that intersects the ellipse plane in a perpendicular manner, ii) Projection of the real measured values whose assigned real beams start from the intersection point, along these beams to the virtual planar detector surface, iii) Determination of a real beam that starts from the intersection point, wherein the impingement point of the real beam and the impingement point of the fictitious beam the virtual planar detector surface lie on a straight line that runs parallel to the ortho straight line, iv) Formation of a partial derivation of the real measured values whose assigned real beams start from the intersection point, according to the position of the respective real measured value on the planar virtual detector surface along a straight line that is parallel to the ortho straight line in the place of the real measured value to which the real beam determined in step iii) is assigned, v) Formation of a partial derivation of the real measured values whose assigned real beams have the same impingement point on the planar virtual detector surface and start from different radiation source positions lying on the ortho straight line, according to the radiation source position on the ortho straight line with the aid of John's equation in the place of the real measured value to which the real beam determined in step iii) is assigned, vi) Determination of the fictitious measured value through a Taylor development, wherein the partial derivations determined in iv) and v) are taken into account.

3. A method as claimed in claim 2, wherein to determine the fictitious measured value by means of a Taylor development in step vi), the real measured value to which the real beam determined in step iii) is assigned, the product of the distance between the intersection point and the fictitious radiation source position and the partial derivation formed in step v) and the product from the distance of the intersection points of the fictitious beam and of a beam that is shifted relative to the real beam parallel to the ortho straight line by the distance between the intersection point and the virtual radiation source position on the virtual planar detector surface and the partial derivation formed in step iv)

are added, wherein the resulting sum is the fictitious measured value.

4. A method as claimed in claim 2, wherein the formation of the partial derivation in step v) has the following steps:

α) Determination of radiation source positions on the intersection ellipse that are adjacent to the intersection point, wherein it is assumed that real beams that are emitted from a real radiation source position that is displaced on the helix by an angle relative to the intersection point are emitted from a radiation source that is displaced on the intersection ellipse by the same angle relative to the intersection point, β) Determination of—respectively—a virtual planar detector surface for each radiation source position determined in step α) on the intersection ellipse by turning the detector surface defined in step i) around the rotational axis by an angle of rotation that is equal to the angle by which tile respective radiation source position on the intersection ellipse is displaced relative to the intersection point, γ) Projection of those real measured values whose assigned real beams are emitted from the real radiation source positions determined in step α), along these beams onto the virtual planar detector surface determined for the respective radiation source position, δ) Formation of the partial derivation of the measured values projected in step γ) according to the angular position of the radiation source positions on the intersection ellipse determined in step α), ε) Formation of the partial derivation of the measured values derived in step δ) according to the position of the respective derived measured value on a straight line, oriented parallel to the ortho straight line, on the respective virtual planar detector surface, ζ) Formation of the second partial derivation of the measured value projected in step γ) according to the position of the respective projected measured value on a straight line, oriented parallel to the ortho straight line, on the respective virtual planar detector surface, η) Formation of a first total through addition of those real measured values derived in step ζ) whose assigned real beams are emitted from the intersection point and, on the virtual planar detector surface defined in step i), lie on a straight line that runs parallel to the ellipse plane and through the impingement point of the real beam defined in step iii), and multiplication of the first total by a weighting factor that is proportional to the reciprocal value of half the large axis of the intersection ellipse, ς) Formation of a second total through multiplication of those real measured values derived in step ζ, whose assigned real beams are emitted from the intersection point and, on the virtual planar detector surface defined in step i), lie on a straight line that runs parallel to the ellipse plane and through the impingement point of the real beam defined in step iii), by the respective position on the straight line, and through addition of these measured values, wherein the second total is multiplied by a weighting factor that is proportional to the reciprocal value of half the small axis of the intersection ellipse, to the reciprocal value of the square of half the large axis of the intersection ellipse, and to the position of the respective derived real measured value in a direction oriented parallel to the ortho straight line, ι) Formation of a product through multiplication of the partial derivation formed in step iv) by a weighting factor that is proportional to the reciprocal value of half the small axis of the intersection ellipse, to the reciprocal value of half the large axis of the intersection ellipse, and to the sum of the product of the two half axes of the intersection ellipse and of the square of the position of the impingement point of the real beam determined in step iii) on the virtual planar detector surface defined in step i) on a straight line oriented parallel to the tangent vector determined in step d), κ) Addition of the first total multiplied in step η) by a first weighting factor, the second total multiplied in step ς) by a second weighting factor, and of the product formed in step ι, wherein the resulting sum is the partial derivation according to step v).

5. A computed tomography machine for carrying out the method as claimed in claim 1, with a radiation source for producing a cone-shaped bundle of rays that passes through an examination zone and an object located therein, a drive arrangement to allow the object contained in the examination zone and the radiation source to rotate relative to one another around a rotational axis, and to be displaced parallel to the rotational axis, a detector unit coupled to the radiation source, for the acquisition of real measured values, a computing unit for determining the fictitious measured values from the real measured values, and for reconstructing an object image from the real measured values and the fictitious measured values, a control unit to control the radiation source, the detector unit, the drive arrangement and the computing unit in accordance with the steps of claim 1.

6. Computer program for a control unit to control a radiation source, a detector unit, a drive arrangement and a computing unit of a computed tomography machine for carrying out the method as claimed in claim 1.

* * * * *